United States Patent [19]

Grötsch

[11] Patent Number: 5,288,913
[45] Date of Patent: Feb. 22, 1994

[54] PROCESS FOR THE PREPARATION OF 4,4'-DIHYDROXYDIPHENYL SULFONE

[75] Inventor: Georg Grötsch, Bad Soden am Taunus, Fed. Rep. of Germany

[73] Assignee: Hoechst Aktiengesellschaft, Frankfurt am Main, Fed. Rep. of Germany

[21] Appl. No.: 100,895

[22] Filed: Aug. 2, 1993

Related U.S. Application Data

[63] Continuation of Ser. No. 835,912, Feb. 26, 1992, abandoned.

[30] Foreign Application Priority Data

Aug. 30, 1989 [DE] Fed. Rep. of Germany ....... 3928704

[51] Int. Cl.$^5$ ........................................... C07C 315/00
[52] U.S. Cl. ...................................................... 568/33
[58] Field of Search ........................................... 568/33

[56] References Cited

U.S. PATENT DOCUMENTS 4,162,270  7/1979  Ogata et al. ............................ 568/33
5,041,677  8/1991  Cooker et al. ......................... 568/33

Primary Examiner—Marianne M. Cintins
Assistant Examiner—Margaret J. Page
Attorney, Agent, or Firm—Connolly and Hutz

[57] ABSTRACT

Process for the preparation of 4,4'-dihydroxydiphenyl sulfone in a high yield and high purity by reaction of phenol with a sulfonating agent in a chlorinated aromatic, in which phenol is reacted with a sulfonating agent in ortho-, meta- or para-chlorotoluene or in any desired mixture of these isomeric chlorotoluenes as the inert solvent, at temperatures of from about 100° to about 200° C.

15 Claims, No Drawings

PROCESS FOR THE PREPARATION OF 4,4'-DIHYDROXYDIPHENYL SULFONE

This application is a continuation of application Ser. No. 07/835,912, filed Feb. 26, 1992 now abandoned.

The invention relates to an improved process for the preparation of 4,4'-dihydroxydiphenyl sulfone in a high yield and in high purity by reaction of phenol with a sulfonating agent in a chlorotoluene.

4,4'-Dihydroxydiphenyl sulfone is a useful starting compound for the preparation of high performance plastics, for example polyesters, polyether-sulfones, epoxy resins, polycarbonates or polyurethanes.

In the majority of processes known for the preparation of 4,4'-dihydroxydiphenyl sulfone in a high purity and yield (>90%) from phenol and a sulfonating agent with removal from the circulation of the water formed in the reaction (German Offenlecjungsschrift No. 3,723,401, WO Patent No. 86/6370, Japanese Patent No. 86/36253, German Patent No. 2,708,388), the reaction mixture is concentrated to dryness in vacuo during or after the end of the reaction and the isomerization of 2,4'-dihydroxydiphenyl sulfone to 4,4'-dihydroxydiphenyl sulfone. Because of this measure, these known processes are extremely unsuitable for implementation on an industrial scale.

According to German Offenlegungsschrift No. 3,723,401, molybdic and tungstic acid or heteropoly acids are employed as condensation catalysts, which are removed from the reaction mixture, for example by filtration, when the reaction has ended. The phenolic mother liquor is then concentrated to dryness. Because of this procedure, contamination of the dihydroxydiphenyl sulfone with heavy metals cannot be excluded, so that the quality of the plastics prepared therefrom may be impaired.

According to WO Patent No. 86/6370, the aromatic sulfonic acids employed as catalysts remain in the reaction product during the working up described, because they have a low volatility. Contamination of the reaction product with these products therefore cannot be reliably excluded.

The process described in German Patent No. 2,804,080 (reaction of phenol with $SO_3$ in liquid hydrogen fluoride) requires an involved, expensive fitting out with apparatus, because of the use of hydrogen fluoride, and is therefore not economically advantageous.

According to European Laid-Open Specification No. 0,220,004, 4,4'-dihydroxydiphenyl sulfone is prepared in a purity of 93%–95% by a process which avoids the abovementioned disadvantage of distillation to dryness. In the reaction of phenol with sulfuric acid in the presence of a di- or trichlorobenzene or a mixture of these solvents, 4,4'-dihydroxydiphenyl sulfone largely crystallizes selectively out of the reaction mixture. However, the yield is unsatisfactory, at a maximum of 82%. A large proportion of the material employed or formed remains in the solvent and must be disposed of expensively.

According to European Laid-Open Specification No. 0,293,037, 4,4'-dihydroxydiphenyl sulfone is obtained by reaction of phenol with sulfuric acid in a suspending agent (isoparaffin) and another solvent which forms an azeotrope with water (likewise an isoparaffin). The yield determined in the reaction mixture by high performance liquid chromatography is not more than 96%. The reaction time stated in that specification is, however, 16 h, which means that the profitability of the process is greatly reduced; no isolated yield is mentioned.

There was thus still a need for an advantageous process, which can be realized industrially without problems, for the preparation of 4,4'-dihydroxydiphenyl sulfone in high purity and at the same time a high yield.

It has now been found, surprisingly, that 4,4'-dihydroxydiphenyl sulfone can be prepared in a high yield and high purity by reaction of phenol with a sulfonating agent in a chlorinated aromatic, by reacting phenol with a sulfonating agent in ortho-, meta- or para-chlorotoluene or in any desired mixture of these isomeric chlorotoluenes as the inert solvent, at temperatures of from about 100° to about 200° C., preferably from about 110° to about 170° C.

Examples of suitable sulfonating agents are the following: above all about 20 to about 80% strength, preferably about 40 to about 70% strength, oleum; furthermore about 70 to about 100% strength sulfuric acid in the presence of a perfluoroalkanesulfonic acid, such as, for example, trifluoromethane- or hexafluoropropanesulfonic acid (in an amount of from about 0.01 to about 10 mol%, based on the sulfuric acid employed, as the sulfonating agent), and the other known sulfonating agents, such as, for example, chlorosulfonic acid, the intermediately formed phenolsulfonic acid or sulfuric acid in the presence of aromatic sulfonic acids.

In the process according to the invention, 1 mole of phenol is an a rule and advantageously reacted with an amount of sulfonating agent which corresponds to about 0.80 to about 0.25, preferably about 0.6 to about 0.4, mole equivalent of $SO_3$. If 1 mole of phenol is reacted with a sulfonating agent in an amount of less than 0.5 mole equivalent of $SO_3$ in the context of the ranges of amounts stated above as advantageous, the yield of 4,4'-dihydroxydiphenyl sulfone in percent of theory relates to the sulfonating agent employed in less than the equivalent amount.

The chlorotoluenes or mixtures thereof used as inert solvents (reaction medium) are as a rule employed in an amount of from about 50 to about 200% by weight, preferably from about 70 to about 130% by weight, based on the amount of 4,4'-dihydroxydiphenyl sulfone to be expected in theory.

The water of reaction formed is removed continuously from the circulation with chlorotoluene, and after separation of the phases in a water separator the solvent is recycled continuously into the reaction mixture. However, it is also possible to top up the chlorotoluene at the rate at which it is removed from the reaction mixture.

4,4'-Dihydroxydiphenyl sulfone is obtained in crystalline form by the process according to the invention and can be separated off directly, for example filtered off, from the reaction mixture.

However, it can also be isolated by removing the inert solvent by means of a steam distillation or an azeotropic distillation with the addition of water. The 4,4'-dihydroxydiphenyl sulfone is obtained in this way as a suspension in water and can then likewise be isolated by filtration.

The process according to the invention can be carried out not only under normal pressure but also under increased pressure or reduced pressure (vacuum).

The process according to the invention has the following advantages over the known preparation methods:

No heavy metal compounds are employed as catalysts, so that corresponding contamination of the product or effluent is reliably excluded, which is necessary amongst other things for ecological reasons.

The reaction mixture does not have to be concentrated to dryness in order to obtain 4,4'-dihydroxydiphenyl sulfone in high purity. All the problems associated with solidification of the distillation bottom product in the reaction vessel, such as, for example, the need for renewed dissolving or melting or mechanical removal of solid product from the reaction vessel, are in this way avoided. This means a lower expenditure on apparatus and therefore lower costs. The catalyst employed moreover does not remain in the product during working up in the manner described, as would be the case if the mixture were concentrated to dryness.

Compared with the procedure according to European Patent No. 0,220,004 (yield according to Example 2: 82%, based on the phenol), the yield is considerably improved (95%, based on the phenol) at a comparable purity.

The use of chlorotoluene instead of chlorobenzene or dichlorobenzenes leads to a significant improvement in the purity of the product by more than 10% (cf. Examples 3 and 4). This is surprising to the expert, since chlorotoluene has previously been described as the solvent only for those processes in which the reaction mixture is concentrated to dryness (WO Patent No. 86/6370, Example 5; German Patent No. 2,708,388, no example). It accordingly had to be assumed that chlorotoluene is not superior to the other customary solvents in the preparation of 4,4'-dihydroxydiphenyl sulfone which is as pure as possible.

The reaction times are shortened to about half in comparison with the use of an isoparaffin mixture, which means that the economic efficiency is increased. The chlorotoluene simultaneously serves for azeotropic removal of the water from the circulation and as an inert solvent, so that no solvent mixture has to be employed. In addition, no isolated yields are mentioned in European Laid-Open Specification No. 0,293,037. Comparison of the purity and yield of the isolated goods with the high performance liquid chromatography yields is scarcely possible.

The invention is illustrated in more detail by the following examples, without being limited to these.

EXAMPLE 1

89 g of 65% strength oleum were added to 188 g of molten phenol, a temperature of about 120° C. being reached. After addition of 225 g of o-chlorotoluene, a total of 23 g of water were removed from the circulation by increasing the reaction temperature to about 150° C. in the course of about 9 h. (When about half of this amount of water to be expected in theory has been removed, 4,4'-dihydroxydiphenyl sulfone starts to crystallize out.) When the reaction had ended, water was added and the o-chlorotoluene was removed in an azeotropic distillation. The crystals now suspended in water were filtered off with suction, washed with water and dried. 237 g of reaction product were obtained, which corresponds to a yield of 95% of theory, based on the phenol. The content of 4,4'-dihydroxydiphenyl sulfone (high performance liquid chromatography) was 93% by area.

EXAMPLE 2

188 g of phenol were reacted with 89 g of 65% strength oleum in the presence of 225 g of p-chlorotoluene analogously to Example 1. 232 g of reaction product were obtained, which corresponds to a yield of 93% of theory, based on the phenol. The content of 4,4'-dihydroxydiphenyl sulfone (high performance liquid chromatography) was 94% by area.

EXAMPLE 3

Comparison Example Using Chlorobenzene Instead of Chlorotoluene 188 g of phenol were reacted with 89 g of 65% strength oleum in the presence of 208 g of chlorobenzene analogously to Example 1. 201 g of reaction product were obtained, which corresponds to a yield of 80% of theory, based on the phenol. The content of 4,4'-dihydroxydiphenyl sulfone (high performance liquid chromatography) was 82% by area.

EXAMPLE 4

Comparison Example Using o-Dichlorobenzene Instead of Chlorotoluene)

188 g of phenol were reacted with 89 g of 65% strength oleum in the presence of 272 g of o-dichlorobenzene analogously to Example 1. When the reaction had ended, the 4,4'-dihydroxydiphenyl sulfone formed was filtered off directly from the reaction mixture with suction. 234 g of reaction product were obtained, which corresponds to a yield of 93% of theory, based on the phenol. The content of 4,4'-dihydroxydiphenyl sulfone (high performance liquid chromatography) was 79% by area.

EXAMPLE 5

102 g of 96% strength sulfuric acid were added dropwise to 188 g of phenol at 130° C. 225 g of o-chlorotoluene and 4.6 g of 2-hydrohexafluoropropanesulfonic acid were then added. Water was removed from the circulation, while increasing the reaction temperature to 150° C. (When about half the amount of water to be expected in theory, of 40 g, has distilled off, 4,4'-dihydroxydiphenyl sulfone starts to crystallize out.) After the end of the reaction (40 g of water have been removed; the reaction time was about 7 hours), o-chlorotoluene was removed quantitatively in azeotropic distillation by addition of 900 .9 of water, 260 g of water also being driven over at the same time. After cooling to room temperature, the precipitate was filtered off with suction, washed with water and dried.

233 g of reaction product were obtained,, which corresponds to a yield of 93% of theory, based on the phenol. The content of 4,4'-dihydroxydiphenyl sulfone (high performance liquid chromatography) was 93% by area.

EXAMPLE 6

188 g of phenol were reacted with 89 g of 65% strength oleum in the presence of 230 g of m-chlorotoluene analogously to Example 1. 234 g of reaction product were obtained, which corresponds to a yield of 94% of theory, based on the phenol. The content of 4,4'-dihydroxydiphenyl sulfone (high performance liquid chromatography) was 93% by area.

EXAMPLE 7

188 g of phenol were reacted with 89 g of 65% strength oleum in the presence of 230 g of chlorotoluene (composition: 49% of o-, 1% of m- and 50% of p-isomer) analogously to Example 1. The yield and purity of 4,4'-dihydroxydiphenyl sulfone correspond to Example 1.

I claim:

1. A process for the preparation of 4,4'-dihydroxydiphenyl sulfone in a high yield and high purity by reaction of phenol with a sulfonating agent, said process comprising:
   carrying out the reaction between phenol and the sulfonating agent in a liquid reaction medium comprising an inert solvent consisting essentially of about 50 to about 200% by weight, based on the amount of 4,4'-dihydroxydiphenylsulfone to be expected in theory, of ortho-, meta- or para-chlorotoluene or a mixture of said chlorotoluenes, at a temperature of from about 100° to about 200° C., and removing the water formed by the reaction continuously from circulation with the chlorotoluene in the reaction medium, until the 4,4'-dihydroxydiphenyl sulfone crystallizes out of the reaction medium, then separating said 4,4'-dihydroxydiphenyl sulfone from the liquid reaction medium.

2. The process as claimed in claim 1, wherein the reaction is carried out at a temperature of from about 110° to about 170°.

3. The process as claimed in claim 1, wherein the chlorotoluene or mixture of chlorotoluenes is employed in the amount of from about 70 to 130% by weight, based on the amount of 4,4'-dihydroxydiphenyl sulfone to be expected in theory.

4. The process as claimed in claim 3, wherein the reaction is carried out at a temperature from about 110° to about 170° C.

5. The process as claimed in claim 3, wherein the sulfonating agent is selected from the group consisting of:
   about 20 to about 80% strength oleum, about 70 to 100% strength sulfonic acid, chlorosulfonic acid, and phenolsulfonic acid.

6. The process as claimed in claim 3, wherein each mole of phenol is reacted with an amount of sulfonating agent which corresponds to about 0.80 to about 0.25 mole equivalent of $SO_3$.

7. The process as claimed in claim 1, wherein said sulfonating agent is selected from the group consisting of: about 20 to 80% strength oleum, about 70 to 100% strength sulfuric acid, chlorosulfonic acid, and phenolsulfonic acid.

8. The process as claimed in claim 1, wherein each mole of phenol is reacted with an amount of sulfonating agent which corresponds to about 0.80 to about 0.25 mole equivalent of $SO_3$.

9. The process as claimed in claim 1, wherein each mole of phenol is reacted with an amount of sulfonating agent which corresponds to about 0.6 to about 0.4 mole equivalent of $SO_3$.

10. The process as claimed in claim 1, wherein the reaction is carried out under normal pressure, increased pressure, or reduced pressure.

11. The process as claimed in claim 1, wherein water formed during the reaction is removed until 4,4'-dihydroxydiphenyl sulfone starts to crystallize out, and when the reaction has ended, water is added, the inert solvent is removed, and the crystallized 4,4'-dihydroxydiphenyl sulfone, now suspended in water, is separated from the water.

12. The process as claimed in claim 11, wherein the reaction is carried out at a temperature of from about 110° to about 170° C.

13. The process as claimed in claim 11, wherein the sulfonating agent is selected from the group consisting of:
   about 20 to about 80% strength oleum, about 70 to 100% strength sulfuric acid, chlorosulfonic acid, and phenolsulfonic acid.

14. The process as claimed in claim 11, wherein each mole of phenol is reacted with an amount of sulfonating agent which corresponds to about 0.80 to about 0.25 mole equivalent of $SO_3$.

15. The process as claimed in claim 14, wherein said amount of sulfonating agent corresponds to about 0.6 to about 0.4 mole equivalent of $SO_3$.

* * * * *